United States Patent [19]

Resnick

[11] 4,320,144
[45] Mar. 16, 1982

[54] FUNGICIDAL USE OF DIPHENYL ESTERS OF ALKYLENES

[75] Inventor: Bruce M. Resnick, West Paterson, N.J.

[73] Assignee: GAF Corporation, New York, N.Y.

[21] Appl. No.: 250,469

[22] Filed: Apr. 3, 1981

[51] Int. Cl.³ .................. A01N 37/02; A01N 37/06
[52] U.S. Cl. .................... 424/311; 424/314; 560/138; 560/140; 560/205
[58] Field of Search ............... 560/138, 140; 424/311, 424/314

[56] References Cited

FOREIGN PATENT DOCUMENTS 738954 10/1955 United Kingdom ............... 560/140

Primary Examiner—Natalie Trousof
Assistant Examiner—Frederick W. Pepper
Attorney, Agent, or Firm—James Magee, Jr.; Marilyn J. Maue

[57] ABSTRACT

The alkylene diphenyl ester compounds having the formula

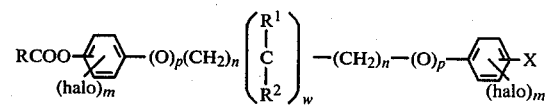

wherein halo is fluorine, chlorine or bromine; R is a radical having not more than 4 carbon atoms, selected from the group consisting of alkenyl, haloalkenyl and haloalkyl; $R^1$ and $R^2$ are each independently hydrogen or methyl; X is hydroxy or the radical RCOO—; m has a value of from 0 to 2; n has a value of from 0 to 6; w and p have values of 0 or 1, except that w is 1 when n is zero; the application of said compounds to plant in amounts sufficient to control fungi infestation and application of mixtures of said compounds to plants.

8 Claims, No Drawings

FUNGICIDAL USE OF DIPHENYL ESTERS OF ALKYLENES

This invention relates to novel diphenyl esters of alkylenes and their use as broad spectrum fungicides for eradication and protection against infestation by plant pathogens.

The effective mycological inhibition evidenced by differentiated chemical species is a complex function of a number of variables including specific activity, resistance to weathering, the type of plant treated, the degree of infestation and varying levels of phytotoxicity. Ecological considerations have barred the use of many effective fungicides because of their persistent residues and toxicity to humans by prolonged ingestation of food crops. To be commercially acceptable current fungicides must leave no toxic residue, they must be easily handled, operate consistently within a spray schedule and be economical to prepare. The foregoing requirements limit the selection of totally acceptable, effective fungicidal agents to a relatively small number of compounds. While many of the available materials comprise complex molecules of specific functionality, most are difficult or expensive to prepare and many of these materials, while effective against one fungicidal species, e.g. rusts, are not effective against other species, e.g. mildew or anthracnose. Such highly specialized fungicides necessitate the use of several sprays for controlling multifungicidal infestation; thus, increasing the amount of residue remaining on the plant or in the soil.

Accordingly, it is an object of the present invention to provide an effective broad spectrum fungicide for the control of mildews, rusts and anthracnose, suitable for application to plants and particularly suitable for food crops since, under normal conditions, these compounds leave no toxic residue.

Another object is to provide novel compounds which have several biocidal uses.

It is another object of the present invention to provide effective mycological agents which are economical to prepare and convenient to use.

In accordance with the present invention, there is provided a broad spectrum, fungicidally effective diphenyl esters of alkylene compounds having the formula:

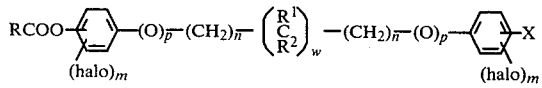

wherein halo is fluorine, chlorine or bromine; R is a radical having not more than 4 carbon atoms, selected from the group consisting of alkenyl, haloalkenyl and haloalkyl; $R^1$ and $R^2$ are each independently hydrogen or methyl; X is hydroxy or the radical RCOO—; m has a value of from 0 to 2; n has a value of from 0 to 6; w and p have values of 0 or 1, except that w is 1 when n is zero. Mono-unsaturated and halo-substituted radicals having the functional moiety at their terminal carbon atoms are preferred. It is also to be understood that mixtures of the above diester compounds may be employed in the operation of the present invention.

In general the diphenyl esters of the present invention are prepared by reacting an organic acid halide, e.g. an unsaturated acyl halide optionally substituted with halogen or a halogenated carboxylic acid halide with an alkylene diphenol or an alkoxylated diphenol, in the presence of a base such as for example triethylamine, sodium carbonate, pyridine, etc. and a solvent selected from the group consisting of methylene chloride, toluene, xylene, benzene or a liquid aliphatic hydrocarbon such as heptane, octane, cyclohexane, or any other conventional inert organic solvent. The reaction can be carried out at a temperature of from about $-25°$ C. to about $20°$ C. under atmospheric pressure for a period of from about 0.5 to about 2 hours. The organic layer is washed with water to extract the halide salt by-product, dried over a desiccant, e.g. magnesium sulfate, filtered to remove desiccant and vacuum distilled to remove solvent.

The product is recovered in a high yield and purity, for example, there is obtained at least 80% conversion of which about 90% is the desired product.

The haloalkyl esters of the alkylene diphenols are prepared by reacting the corresponding halogenated carboxylic acid halide with an above defined alkylene diphenol or alkoxylated diphenol at a temperature of from about $-25°$ C. to about $20°$ C. under atmospheric pressure. Other methods of preparation will become apparent to those skilled in the art from the above discussion of desirable compounds and the above described reaction conditions. Examples of suitable halogenated carboxylic acid halides include the chlorides or bromides of 2-chloroacetic; 3-chloropropionic; 4-bromobutyric; 2,2-dichloroacetic; 2,3-dichloropropionic; 3-trifluoromethyl propionic, and 2,3,4-trichlorobutyric acids and other mono- and polyhalogenated carboxylic acid halides.

Examples of polyhydroxy biphenyl reactants which can be used in the process for preparing the compounds of the present invention are those having the formula:

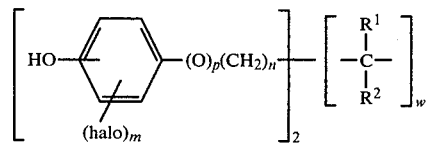

wherein halo, $R^1$, $R^2$, m, n, p and w are as defined above and mixtures thereof.

Examples of the above alkylene diphenol reactants include bis(4-hydroxy-2-chlorophenyl)methane; 1,3-bis[(4-hydroxy-2-bromophenyl)oxy] propane; 1,4-bis[(4-hydroxy-2-fluorophenyl)oxy] butane; 1,6-bis[(4-hydroxy-2,6-bis[(4-hydroxy-2,6-dichlorophenyl)oxy]-hexane; 1,2-bis[(2-hydroxyphenyl)oxy] ethane; bis[3-hydroxy-6-chlorophenyl)oxy] methane; 1,4-bis[(4-hydroxy-2,5-difluorophenyl)oxy] butane; 1,2-bis[(4-hydroxy-2,5-dibromophenyl)oxy] ethane; bis[(4-hydroxyphenyl)oxy] methane; 1,3-bis[(3-hydroxyphenyl)oxy] propane; bis[(4-hydroxy-2-bromophenyl)oxy] methane; 2,2-bis(4-hydroxyphenyl) propane; 2,2-bis(2-hydroxy-4-fluorophenyl)ethane; bis(3-hydroxyphenyl)methane; 1,5-bis[(4-hydroxyphenyl)oxy] pentane; 1,5-bis[(4-hydroxyphenyl)oxy]-3-methylpentane; 1,5-bis[(2-hydroxyphenyl)oxy]-3,3-dimethylpentane; 1,9-bis[(3-hydroxyphenyl)oxy]nonane; 1,3-bis[(3-hydroxy-2,6-dichlorophenyl)oxy] propane; 1,9bis[(4-hydroxy-2,5-dibromophenyl)oxy]-5-methylnonane; 1,7-bis[(4-hydroxy-2-fluorophenyl)oxy]-heptane; 1,13-bis[(4-hydroxyphenyl)oxy] tridecane and isomer and haloanalogs thereof.

The unsaturated acyl halide of the above reaction is defined as having the structure

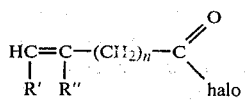

wherein R' is hydrogen, chlorine or bromine; R" is hydrogen or methyl; n has a value of 0 to 2 and halo is chlorine or bromine. Of this group acryloyl chloride and methacryloyl chloride are most preferred.

Representative of the products of this invention are the following:
bis(4-methacryloyloxyphenyl) methane;
bis(4-acryloyloxy-2-chlorophenyl) methane;
bis(2-acryloyloxyphenyl) methane;
2,2-bis(3-acryloyloxyphenyl) ethane;
2,2-bis(4-acryloyloxyphenyl) propane;
2,2-bis(4-methacryloyloxyphenyl) propane;
bis[(4-acryloyloxy-2,6-dichlorophenyl)oxy] methane;
1,3-bis[(4-acryloyloxy-3-fluorophenyl)oxy] propane;
1,4-bis[(4-acryloyloxy-2-bromophenyl)oxy] butane;
1,5-bis[(4-acryloyloxy-2,6-dichlorophenyl)oxy] pentane;
1,8-bis[(3-methacryloyloxyphenyl)oxy] octane;
1,9-bis[(3-acryloyloxyphenyl)oxy] nonane;
1,8-bis[(3-methacryloyloxy-2,4-dichlorophenyl)oxy] octane;
bis(4-methacryloyloxy-3-chlorophenyl) methane;
1,4-bis[(4-methacryloyloxy-2-bromophenyl)oxy] butane;
1,2-bis[(4-methacryloyloxy-2-fluorophenyl)oxy] ethane;
bis[(4-methacryloyloxy-2,6-dichlorophenyl)oxy] methane;
1,7-bis[(4-methacryloyloxy-2,6-dibromophenyl)oxy] heptane;
1,3-bis[(4-methacryloyloxy-phenyl)oxy] propane;
2,2-bis[(4-chloroacetoxy-3-fluorophenyl)oxy] ethane;
1,4-bis[(4-chloroacetoxy-2-bromophenyl)oxy] butane;
1,5-bis[(3-chloroacetoxyphenyl)oxy] pentane;
1,5-bis[(3-dichloropropanoyloxyphenyl)oxy] pentane;
1,8bis[(3-dibromopropanoyloxyphenyl)oxy] octane;
1,5-bis(4-dichlorobutanoyloxy-2-chlorophenyl) pentane;
1,8-bis(4-dibromobutanoyloxyphenyl) octane;
1,5-bis[(4-dichlorobutanoyloxyphenyl)oxy] pentane;
and isomers and haloanalogs thereof.

The diphenyl diesters of the present invention effect inhibition of widely variant plant pathogens and may be generally used in the control of infestations on many species of plants by application prior to infestation as a protectant or after infestation to retard established growth. Although the present products may be applied in full strength, directly to a plant or plant part for economy and better distribution, the product is preferably applied in diluted form as a liquid solution or dispersion or as particulate solid or a dust. Suitable liquid carriers for the present products include water and organic solvents such as isopropanol, ethyleneglycol, acetone, benzene, toluene, polyethylene glycol, polypropylene glycol, and other conventional inert carriers. Exemplary of the solid carriers suitably employed with the present products are talc, bentonite, diatomaceous earth clays, and the like.

The concentration of the active fungicide varies with the species of plant treated, the mycological species sought to be controlled, climatic conditions and the particular fungicide employed; however, the present products are usually applied in a concentration of between about 5 and about 300 parts per million, preferably between about 20 and about 250 parts per million, applied to provide coverage of from about 1 to about 30 lbs. per acre, preferably about 3 to about 25 lbs. per acre. In certain cases involving a persistent or heavy fungicidal infestation, it may be desirable to employ solutions up to 500 ppm of the present fungicides.

The fungicidal compositions of the present invention may also be applied to or compounded in or with other substrates susceptible to fungal infestation including wood, paper, leather textiles etc.; however their preferred utility is expressed in the field of agriculture, and particularly in the control of plant pathogens as by foliar application as a liquid spray or dust either to growing crops or processed agricultural products, e.g. picked fruit or vegetables. The present products may also find utility as bacteriocides in household or commercial washing or cleansing solutions.

The fungicidal products can be formulated and applied with carrier or they may be incorporated in available formulations containing other agriculturally active agents such as plant growth regulators, insecticides, fertilizers or herbicides, as are presently marketed. In all cases, the fungicidal compositions of this invention are used in fungicidally effective amounts in the desired formulation. Liquid compositions containing the present fungicides can be applied to plants by spraying to drench, by misting or by immersing picked fruit or vegetables in a fungicidal solution. Also wrappings for fruits and vegetables can be impregnated with the present fungicide/carrier composition to prevent rot or decay during shipment and distribution.

If desired, the present fungicidal compositions may include any of the conventional adjuvants such as surfactants, thickening agents, or sticking agents.

Having generally described the present invention, reference is now had to the accompanying examples which illustrate preferred embodiments but which are not to be construed as limiting the scope of the invention as set forth in the foregoing description and in the appended claims. All amounts and proportions recited in the following examples are by weight unless otherwise indicated.

EXAMPLE A

This example is representative of methods for synthesizing the bis[(acryloyloxyphenyl)oxy]alkanes of the invention. It is to be understood that unsubstituted or halogen substituted acryloyl bromides and chlorides or methacryloyl chlorides and bromides can be substituted herein to provide the corresponding acryloyloxy and methacryloyloxy esters or their halogenated counterparts. Additionally other bis(hydroxyphenyloxy) alkane reactants, such as the corresponding methane, ethane, propane, butane, hexane, heptane, octane, nonane, decane, undecane, dodecane and tridecane or their isomers or phenyl halogenated counterparts can be substituted for bis[(hydroxyphenyl)oxy] pentane herein to provide the products of this invention.

Preparation of 1,5-bis[(3-acryloyloxyphenyl)oxy] pentane

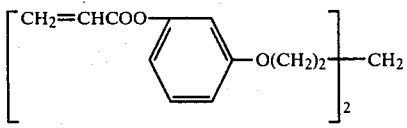

A mixture of 2.9 g of 1,5-bis[(3-hydroxyphenyl)oxy] pentane and 2.1 g of triethylamine was added to 100 ml of dichloromethane in a glass flask. After chilling the solution in an ice bath, 1.8 g of acryloyl chloride in 50 ml of methylene chloride was added dropwise with stirring to maintain the temperature of the reaction mixture below 10° C. The mixture was then stirred for 2 hours, during which the product separates as an oily layer. The oily layer was removed, washed with water, dried over magnesium sulfate and evaporated to dryness, leaving 4 g of oily product (99.0% yield). The product was identified by nuclear magnetic resonance and by mass spectrometry.

In the above example, 1,8-bis[(3-hydroxy-2,4-dichlorophenyl)oxy] octane was substituted for 1,5-bis[(3-hydroxyphenyl)oxy] pentane and methacryloyl bromide was substituted for acryloyl chloride to provide the corresponding product

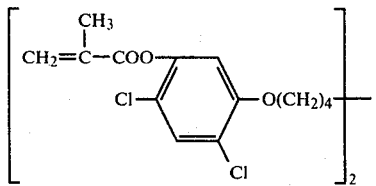

in 90% yield.

Similarly in the above example, bis[(4-hydroxyphenyl)oxy] methane was substituted for 1,5-bis[(3-hydroxyphenyl)oxy] pentane to provide the corresponding product

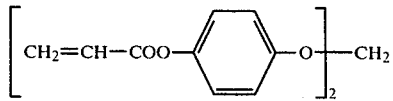

By substituting the 1,5-bis[(4-hydroxyphenyl)oxy] pentane, the 1,8-bis[(4-hydroxy-2,6-dichlorophenyl)oxy] octane or the bis[(3-hydroxyphenyl)oxy] methane isomers, the corresponding isomeric products were produced in at least 85% yield.

Substitution of 3,3-dichloroacryloyl chloride in Example A provides the corresponding product

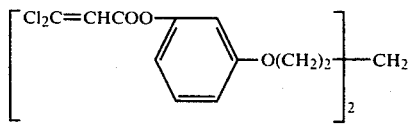

in at least 85% yield.

EXAMPLE B

This example is representative of methods for synthesizing the bis(acryloyloxyphenyl) alkanes of the invention. It is to be understood that unsubstituted or halogen substituted acryloyl chlorides and bromides or methacryloyl chlorides and bromides can be substituted herein to provide the corresponding acryloyloxy and methacryloyloxy esters or the halogenated counterparts of this invention. Additionally other bis(hydroxyphenyl) alkane or bis(hydroxy halogenated phenyl) alkane reactants, such as the corresponding methanes, ethanes, propanes, butanes, pentanes, hexanes, heptanes, octanes, etc. or their isomers can be substituted for 2,2-bis(hydroxyphenyl) propane herein to provide the products of this invention Preparation of 2,2-bis(4-methacryloyloxyphenyl) propane

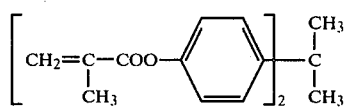

A mixture of 1.14 g. of 2,2-bis(4-hydroxyphenyl) propane in 1.05 g. of triethylamine was added to 100 ml of propanol in a glass flask. To this mixture 1.04 g. of methacryloyl chloride was slowly added and the mixture stirred at 30° C. for 3 hours. The product was separated by filtration, washed with water and dried as in Example A to provide 1.64 g. of product (90% yield). The product was identified by mass spectrometry and nuclear magnetic resonance.

In the above example, acryloyl chloride was substituted for methacryloyl chloride to provide the corresponding ester product

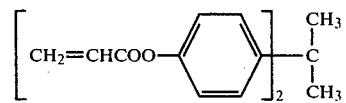

When bis(3-hydroxy-2,4-difluorophenyl) methane is substituted for 2,2-bis(4-hydroxyphenyl) propane and acryloyl bromide is substituted for methacryloyl chloride in the above example, the product

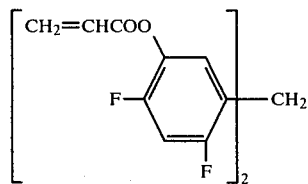

is obtained in at least 85% yield. Similarly, substitution of 3,3-dibromoacryloyl bromide in Example B provides the product

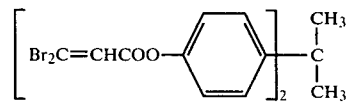

in a yield of at least 85%.

EXAMPLE C

This example is representative of methods for synthesizing the bis[haloalkanoyloxyphenyloxy] alkanes and bis(haloalkanoyloxyphenyl) alkanes of this invention. It is to be understood that any of the halogenated carboxylic acid chlorides or bromides can be substituted herein to produce the corresponding ester products. Additionally, other bis(hydroxyphenyl)-, bis(hydroxy halogenated phenyl)-, bis[(hydroxyphenyl)oxy]- and bis[(hydroxyhalogenated phenyl)oxy]-alkanes, such as the corresponding methanes, ethanes, propanes, butanes, pentanes, hexanes, heptanes, octanes, nonanes, etc. or their isomers can be substituted for 1,5-bis[(4-hydroxyphenyl)oxy] pentane herein to provide the products of this invention.

Preparation of 1,5-bis{[4-(3,3-dichloropropanoyloxy)phenyl]oxy}pentane

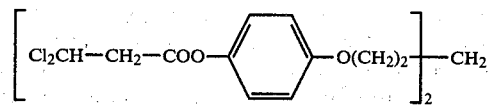

A mixture of 1.43 g. of 1,5-bis[(4-hydroxyphenyl)oxy] pentane in 1.01 g. of triethylamine was added to 125 ml of benzene in a glass flask. The solution was chilled in an ice bath and 1.62 g. of 3,3-dichloropropionic acid chloride was added dropwise with stirring at a temperature of about 5° C. The mixture was stirred for 3 hours with gradual warming to room temperature, after which the product is separated by filtration and is then washed with water, distilled and dried to 1.98 g. of product (85% yield).

In the above example, when 1,4-bis(3-hydroxyphenyl) butane or 2,2′-bis(2-hydroxyphenyl) pentane is substituted for 1,5-bis[(4-hydroxyphenyl)oxy] pentane, the corresponding products

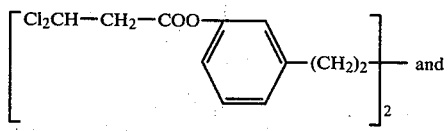 and

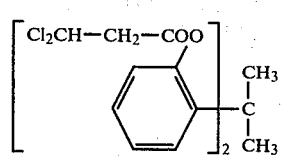

respectively are obtained in at least 80% yield.

Substitution of 2-fluoroacetic acid chloride for 3,3-dichloropropionic acid chloride and 1,5-bis[(4-hydroxy-2,5-difluorophenyl)oxy] pentane in Example C provides the product

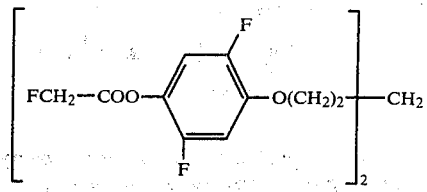

in at least 85% yield.

EXAMPLE D

It will be seen that in each of the above examples and in the substitutions indicated, that by employing half the amount of the acryloyl halide or halogenated carboxylic acid halide reactant, the corresponding monoester hydroxyphenyl products are obtained.

Preparation of 1-(3-acryloyloxyphenyloxy)-5-(3-hydroxyphenyloxy) propane

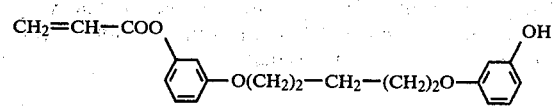

A mixture of 2.9 g. of 1,5-bis[(3-hydroxyphenyl)oxy] pentane and 2.1 g. of triethylamine was added to 100 ml of dichloromethane in a glass flask. After chilling the solution in an ice bath, 0.8 g. of acryloyl chloride was added dropwise to maintain the temperature of the reaction mixture below 10° C. The mixture was stirred for 2 hours and the product separates as an oily layer. The oily layer is recovered, washed with water, dried over magnesium sulfate and evaporated to dryness to provide the desired product in admixture with 10% diacrylate ester in about 60% yield. The mono- and di-esters are separated by distillation, if desired.

EXAMPLE 1

Powdery mildew

The bean powdery mildew is an obligately parasitic fungus that must be transferred directly from infected plants to healthy plants in a relatively dry environment. In the present tests, healthy young bean plants with fully expanded primary leaves in 2½″ pots were placed for 2 days on a greenhouse bench between two rows of infected plants covered with a mass of white, powdery conidia, and exposed to a shower of conidia.

Plants with incipient infection were atomized while rotating on a turntable with an aqueous solution of 250 ppm of test material shown in Table I and the soil was drenched with 21 ml of a 520 ppm solution (at a rate equivalent to 26 lb/acre). The treated plants were then returned to the greenhouse bench near infected plants. After 14 days observations were made on the % arrested of established infection present on the primary leaves at the time of spraying. The plants were reexamined 7 days later for infection on new growth as well as on the primary leaves to determine residual and systemic effects on the fungus. On both occasions the leaves are rated in % control of mildew.

TABLE I

| Test Compound | Chemical Name | % Control of Infestation arrested |
|---|---|---|
| 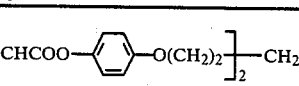 | 2,2-bis(4-methacryloyloxyphenyl) propane | 25 |
|  | 1,9-bis(3-acryloyloxyphenyl) nonane | 45 |
| 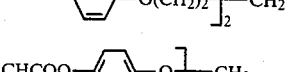 | 1,8-bis(3-methacryloyloxy-4,6-dichlorophenyl) octane | 50 |

EXAMPLE 2

Bean rust (*Uromyces phaseoli*) is representative of a large number of obligate parasites whose prolificacy in generating new parasitic races has frequently frustrated efforts to control them by breeding for disease resistance. The present tests were made with separate aqueous solutions each containing 260 ppm the compounds shown in Table II on Pinto beans grown in 2.5 inch pots for 9 to 12 days by a combination of foliage spray and systemic protection from soil applications. In the test 21 ml of a 520 ppm formulation (equivalent to 25 lb/acre) was poured on the surface of the soil. At the same time the foliage was sprayed with 100 ml of the aqueous solutions containing 260 ppm of the compounds shown in Table I while plants were rotating on a turntable. After the spray deposit had dried, the plants were atomized with a suspension of uredospores (summer spore stage) and placed in a moist chamber at 70° F. for 24 hours. After 7 to 9 days the severity of pustule formation was rated in % control, as compared to untreated controls. The results are reported in following Table II.

The above compounds did not exhibit systemic activity; hence foliar application is recommended.

EXAMPLE 3

Cucumber anthracnose (*Colletotrichum lagenarium*) is a representative of leaf blights caused by the *Fungi Imperfecti*.

Tests were made on cucumber plants grown in 2.5 inch pots for 9-12 days by a combination of foliage spray. In the test, the foliage was sprayed with 100 ml of a 250 ppm aqueous formulation of the compounds reported in Table III as described below. After the spray deposit had dried, the treated plants were inoculated with a suspension of anthracnose conidia in water and placed in a moist chamber at 24° C. for 24 hours. Four days after inoculation, the number of lesions were counted, and % control reported.

TABLE II

| Test Compound | Chemical Name | % Control of Rust Infestation |
|---|---|---|
| 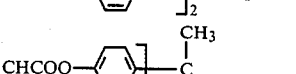 | 1,5-bis[(4-acryloyloxyphenyl)oxy] pentane | 100 |
| | 1,5-bis[(3-acryloyloxyphenyl)oxy] pentane | 100 |
| | bis[(4-acryloyloxyphenyl)oxy] methane | 50 |
| | 2,2-bis(4-acryloyloxyphenyl) propane | 80 |
| 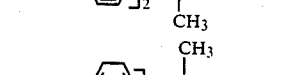 | 2,2-bis(4-methacryloyloxyphenyl) propane | 100 |

TABLE III

| Test Compound | % Control of Anthracnose Infestation |
| --- | --- |
| 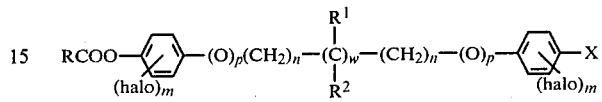 | 90 |
|  | 40 |
|  | 20 |
|  | 90 |
|  | 90 |

As shown in the above tables, the most preferred concentration levels of the present fungicidal compounds fall within the range of between about 150 and about 300 ppm. Other compounds, included within the scope of the present invention may require higher concentrations to achieve maximum effectiveness, e.g., concentrations of up to about 500 ppm. The present compounds are advantageously used on edible crops since they leave no toxic residue and have no systemic effect beyond 2 weeks following application. These properties make the present fungicidal compounds ideal for treatment of picked fruit and vegetables to prevent spoilage in shipment and storage.

It is to be understood that many variations and modifications of the above examples will become apparent to those skilled in the art and are considered to be in the scope of the invention. For example, the present fungicides may be incorporated into solid carriers such as clay, talc, pumice, or bentonite to provide compositions which may be applied either to infested areas on the plant or to areas which may be subjected to infestation. They may also be dissolved in liquified gases such as methyl chloride and applied as aerosol sprays containing the solution. Also, any of the above named monoesters or diesters which are not illustrated in the above examples can be substituted therein to provide similar fungicidal control.

I claim:

1. A method of inhibiting growth of fungi which comprises exposing said fungi to a growth inhibiting quantity of a diphenyl ester having the formula:

$$\text{RCOO} - \underset{(\text{halo})_m}{\bigcirc} - (\text{O})_p (\text{CH}_2)_n - \underset{R^2}{\overset{R^1}{\underset{|}{\overset{|}{C}}}}_w - (\text{CH}_2)_n - (\text{O})_p - \underset{(\text{halo})_m}{\bigcirc} - X$$

wherein halo is fluorine, chlorine or bromine; R is a radical having not more than 4 carbon atoms, selected from the group consisting of alkenyl, halogenated alkenyl and halogenated alkyl; X is hydroxy or the radical RCOO—; $R^1$ and $R^2$ are each independently hydrogen or methyl; m has a value of from 0 to 2; n has a value of from 0 to 6; w and p each have a value of 0 or 1, except that w is 1 when n is zero or a mixture of said esters.

2. The method of claim 1 wherein said ester is applied to a plant in an amount sufficient to prevent or control fungus infestation.

3. The method of claim 1 wherein the X group and the —OOCR group of the ester is an acrylate radical.

4. The method of claim 1 wherein the X group and the —OOCR group of the ester is a methacrylate radical.

5. The method of claim 3 wherein the ester is non-halogenated.

6. The method of claim 1 wherein the compound is employed with an aqueous carrier in a concentration of between about 30 and about 500 ppm.

7. The method of claim 6 wherein the fungus is plant rust.

8. The method of claim 6 wherein the fungus is anthracnose.

* * * * *